United States Patent [19]
Bazin

[11] Patent Number: 6,029,272
[45] Date of Patent: Feb. 29, 2000

[54] SUN VISOR HAVING DETACHABLE BRIM AND MOISTURE ABSORBENT PAD

[76] Inventor: Ferdinand Bazin, 1016 St. Charles Ave., Charlottesville, Va. 22901

[21] Appl. No.: 09/151,151

[22] Filed: Sep. 10, 1998

Related U.S. Application Data

[63] Continuation-in-part of application No. 09/056,175, Apr. 7, 1998, abandoned.
[51] Int. Cl.$^7$ ........................................................ A61F 9/00
[52] U.S. Cl. ........................................................ 2/12; 2/209.3
[58] Field of Search ................................ 2/10, 12, 181, 2/209.3, 171, 209.13

[56] References Cited

U.S. PATENT DOCUMENTS

| | | | |
|---|---|---|---|
| 1,809,956 | 6/1931 | Wrenshall | 2/12 |
| 5,704,063 | 1/1998 | Tilden | 2/12 |

*Primary Examiner*—Diana Oleksa
*Attorney, Agent, or Firm*—Sheldon H. Parker

[57] ABSTRACT

The invention discloses a novel sun visor, and more particularly, to the combination of a sun visor and bandanna, and to the attachment mechanism, for releasably securing the headband to the visor. A sun visor includes a band of flexible, moisture absorbent material, and a sun visor brim member. The brim member is a planar self-supporting material, secured to the band by flaps. The brim is adapted to lie symmetrically curved when affixed to the head of a person by the band. The inner curved edge of the brim is positioned to lie against the forehead of the user, when affixed to the head of a person by the band. Two or three flaps are provided each of which extending inward from the curved inner edge. Each flap is provided with pairs of fasteners, preferably of the hook and loop type, that the flaps can be folded over and secured in the folded position by the fasteners, to form an elongated loop. The brim is preferably a closed cell, substantially moisture impermeable polymeric foam. The flaps are extended approximately perpendicular to a line tangent to the curve of the inner brim edge at the point of intersection of the flap inner edge and the brim inner edge.

16 Claims, 7 Drawing Sheets

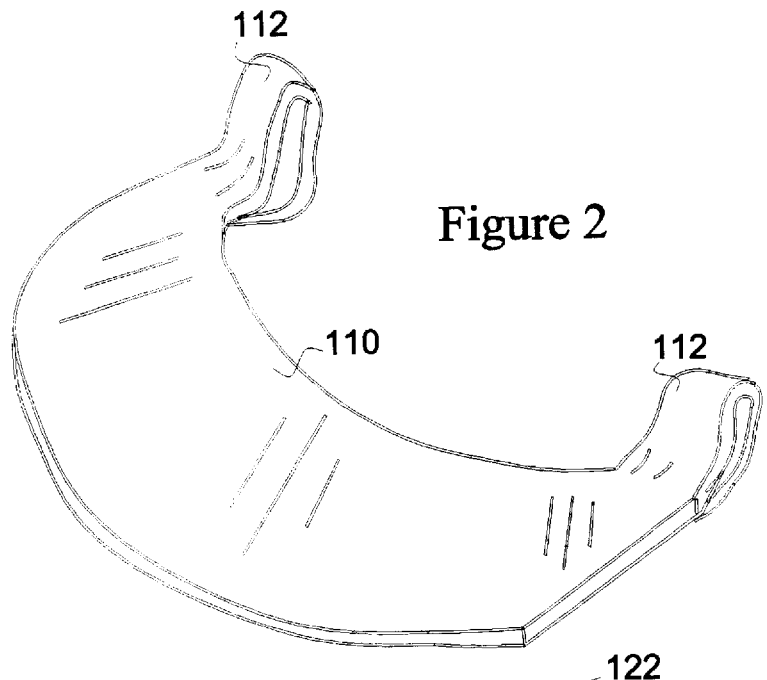
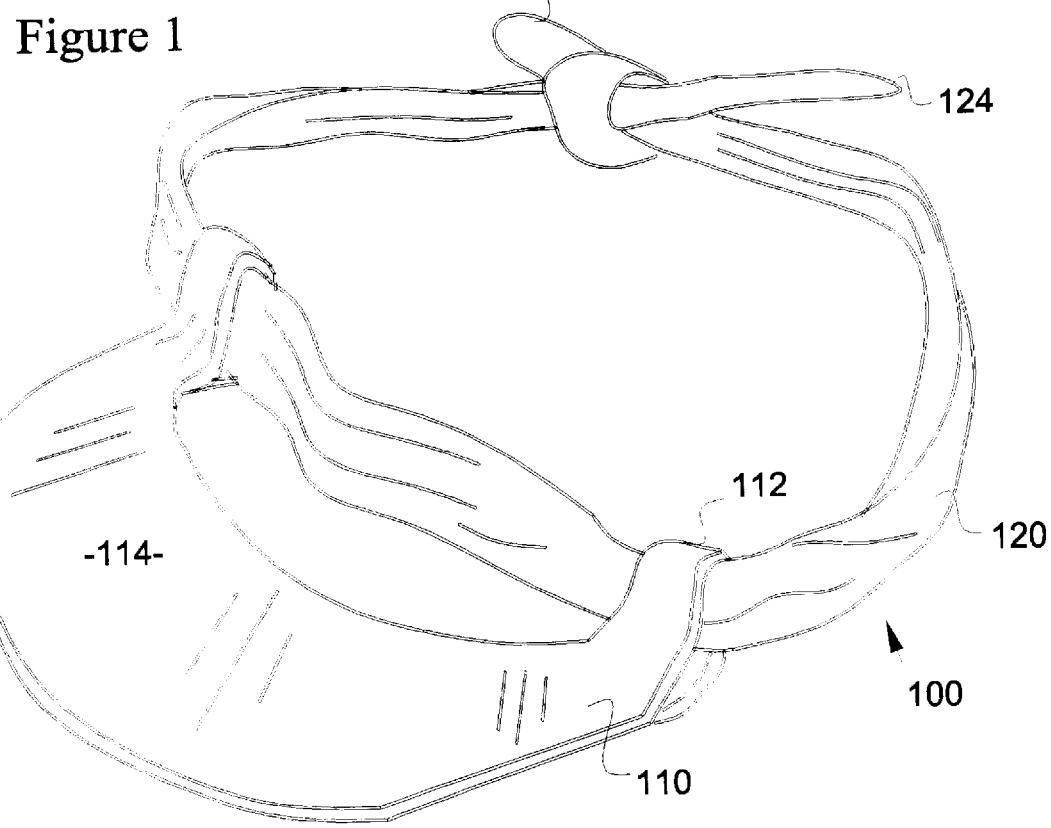

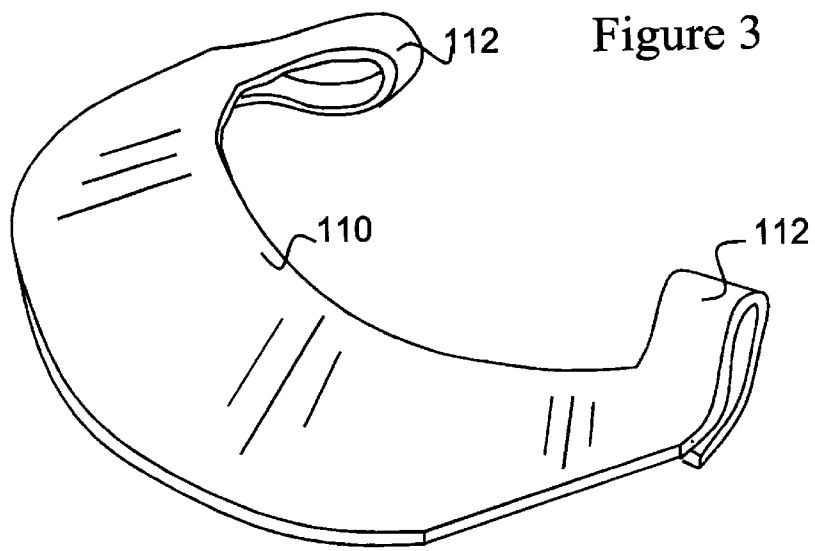
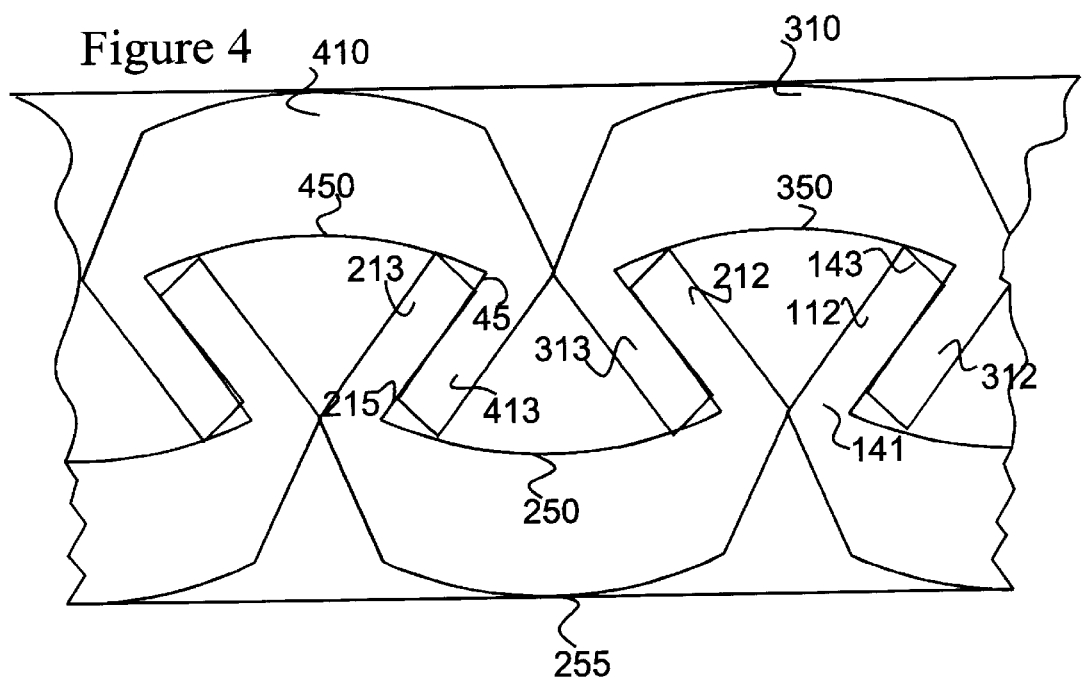

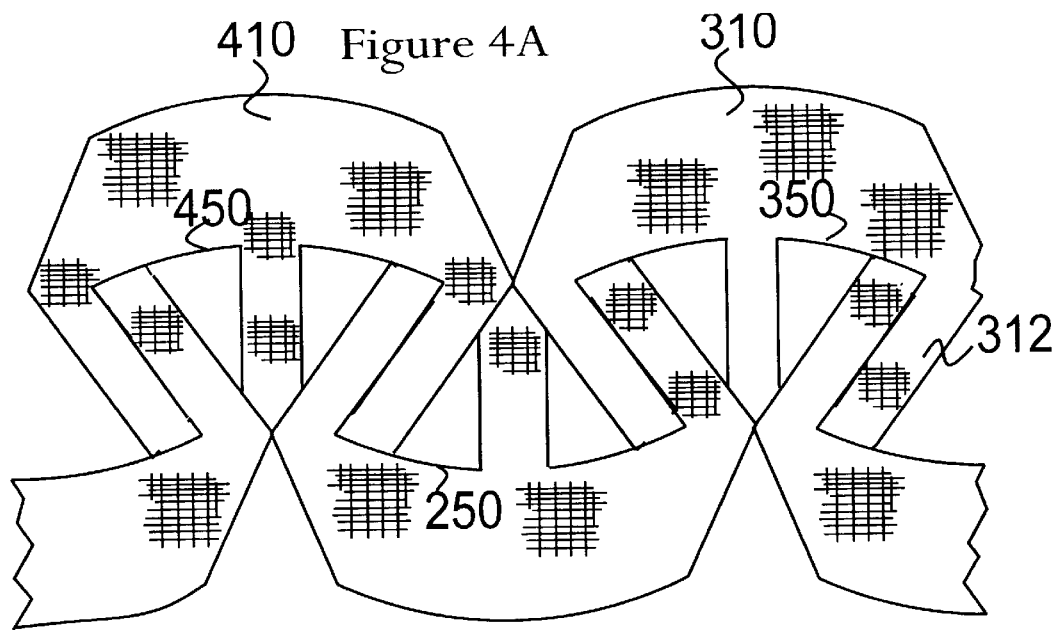
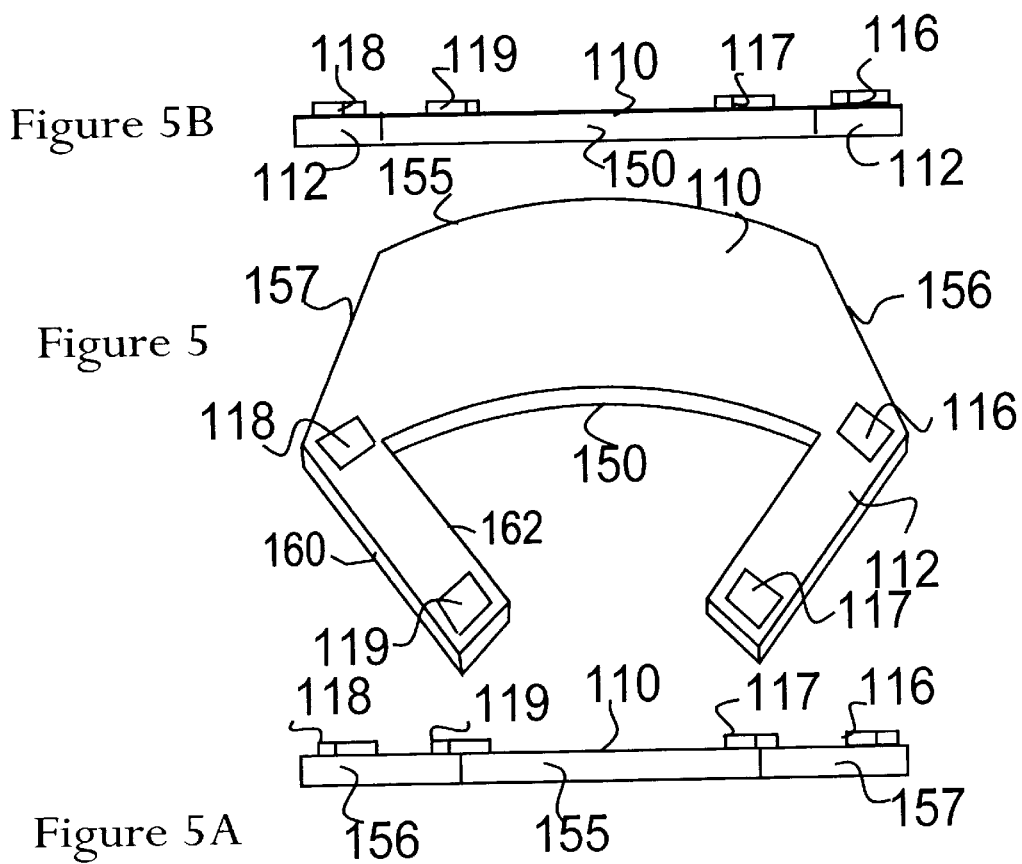

Figure 6
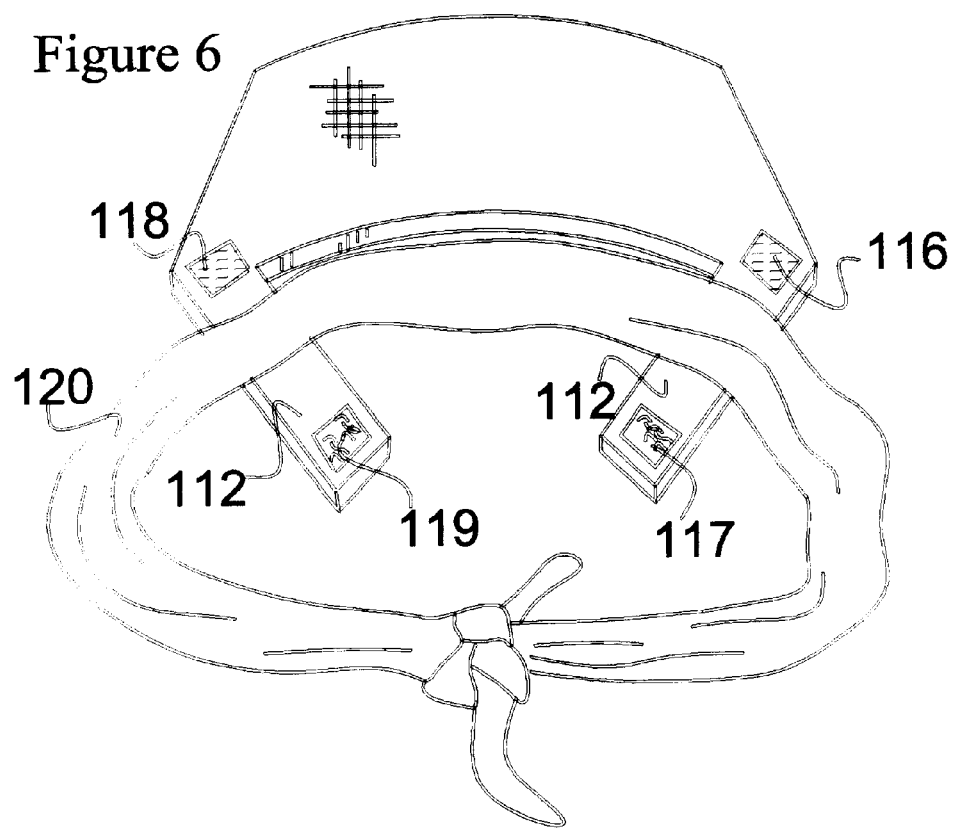
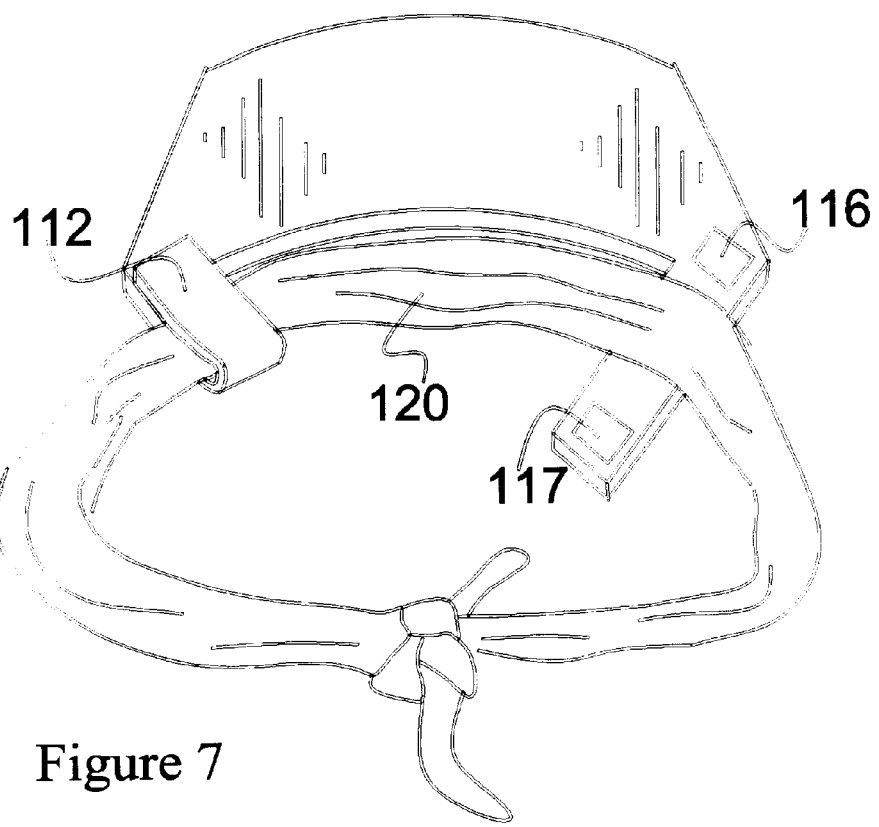
Figure 7

Figure 13
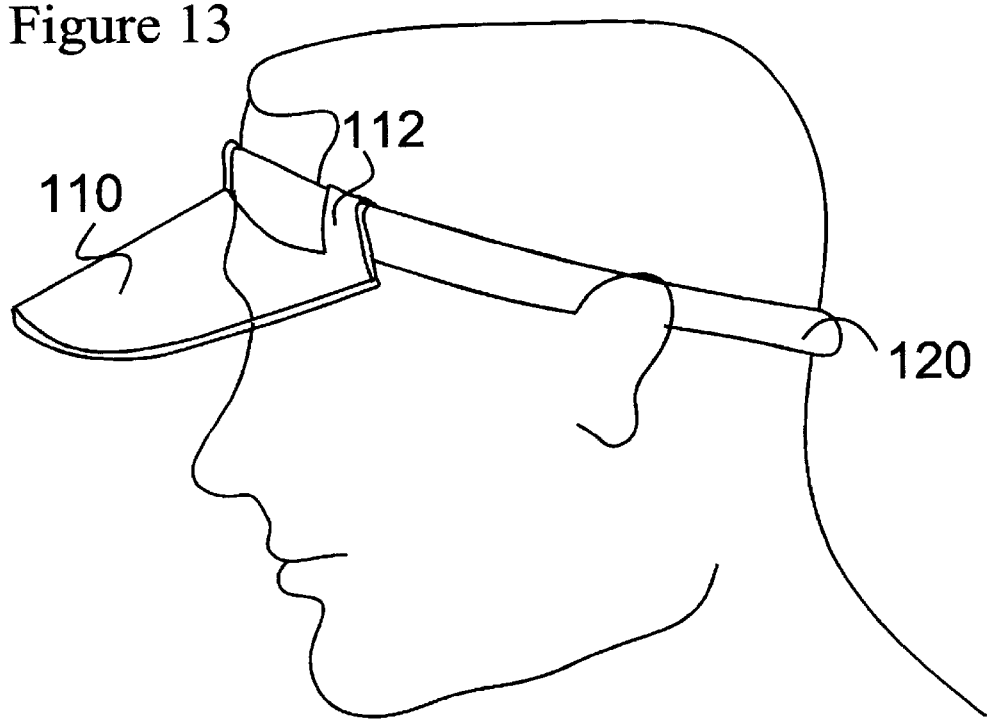
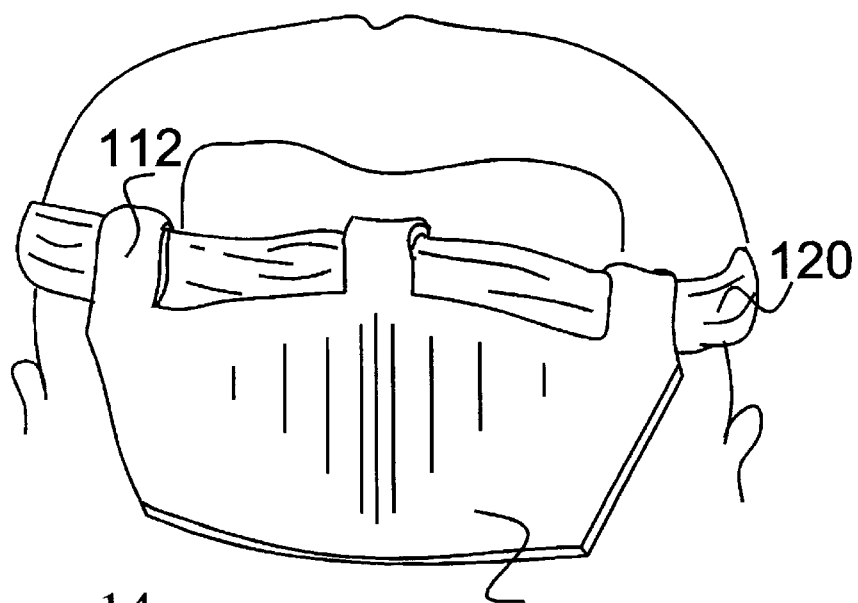
Figure 14

SUN VISOR HAVING DETACHABLE BRIM AND MOISTURE ABSORBENT PAD

CROSS-REFERENCE TO RELATED APPLICATIONS

This application is a continuation in part of patent application 09/056,175, filed Apr. 7, 1998, now abandoned, the disclosure of which is incorporated herein by reference, as though recited in full.

BACKGROUND OF THE INVENTION

1. Field of the Invention

The invention relates to a novel sun visor, and more particularly, to the combination of a sun visor and bandanna or other style of headband, and to the attachment mechanism, for releasably securing the bandanna to the visor.

2. Brief Description of the Prior Art

The use of baseball caps and sweatbands has attained a high level of popularity. A disadvantage of baseball caps, is that they must be washed in a dishwasher or, with some difficulty, in a washing machine, because of the propensity to become stained. Additionally, baseball caps prevent heat from being lost from the top of the head, and therefore can be too warm to wear in hot weather. Sweatbands do not suffer from the shortcomings of baseball caps, but do not shield the eyes from the sun. U.S. Pat. No. 1,809,956, discloses the combination of an eye shield or visor and a bandanna. The combination provides the advantage that the bandanna functions as a perspiration absorbing pad and can be expeditiously removed when it is desired to launder the bandanna or to replace it with another bandanna. The bandanna is secured to the visor by three eyes. The visor is securely supported in position in spaced relation to the head of the wearer and only the eyes (2) of FIG. 1, come into contact with the user, thereby protecting the visor from the user's perspiration. FIG. 4 shows the visor to be downwardly sloping and curved. The visor shape illustrated in FIG. 1, cannot be curved to conform to the cross-sectional view illustrated in FIG. 4. Thus, the concept of the '956 patent is interesting, but the patent discloses a two dimensional representation of a design which cannot be reproduced in a three dimensional product.

It is the object of the present invention to produce a low cost sun visor which is simple to manufacture and which overcomes the shortcomings of the prior art.

BRIEF DESCRIPTION OF THE DRAWINGS

FIG. 1 is a perspective view of the sun visor and bandanna combination of the instant invention;

FIG. 2, is a perspective view of the sun visor of FIG. 1, without a headband;

FIG. 3, is a perspective view of the sun visor of FIG. 1, showing the bandana receiving elements of the visor, in the folded position;

FIG. 4, is a plan view of a series of nested visor patterns on a roll of visor fabric;

FIG. 4A, is a plan view of a series of nested visor patterns, having three flaps, on a roll of visor fabric;

FIG. 5, is a top perspective view of the sun visor of the instant invention;

FIG. 5a is an end view of the sun visor of FIG. 5, when viewed from the brim end of the visor;

FIG. 5b is an end view of the sun visor of FIG. 5, when viewed from the flap end of the visor;

FIG. 6, is a plan view of the sun visor of FIG. 5, with a tied bandanna positioned on the visor;

FIG. 7, is a plan view of the sun visor and bandanna of FIG. 6, showing one bandanna holding flap, in the folded over position;

FIG. 13 is a side view of a three flap sun visor, shown on the head of a user; and FIG. 14 is a front perspective view of the head band visor of FIG. 13.

SUMMARY OF THE INVENTION

Figure 10:
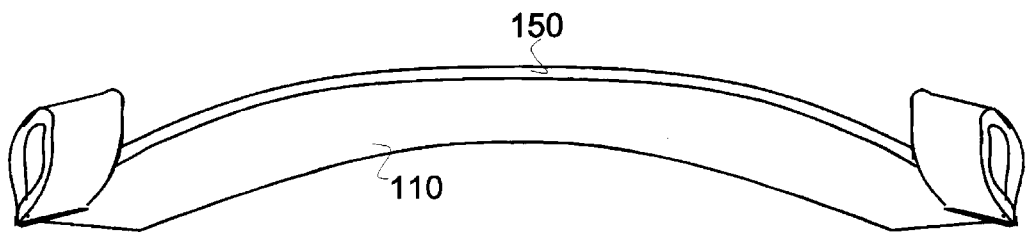
FIG. 10 is a rear perspective view of the sun visor of FIG. 8, showing the curvature of the brim.

The invention relates to a novel sun visor, and more particularly, to the combination of a sun visor and bandanna, and to the attachment mechanism, for releasably securing the headband to the visor.

A sun visor includes a band of flexible, moisture absorbent material, and a sun visor brim member. The brim member is a planar self-supporting material, secured to the band by flaps. The brim is adapted to lie symmetrically curved when affixed to the head of a person by the band. The brim has an inner curved edge positioned to lie against the forehead of the user, when said brim member is affixed to the head of a person by the band. Two or three flaps are provided each of which extending radially inward from the curved inner edge and having a length in the range from about 5 cm to 10 cm.

Pairs of fasteners, preferably of the hook and loop type, are provided for each flap such that the flaps can be folded over and secured in the folded position by the fasteners, to form an elongated loop. Each flap has a preferred length in the range from about 6 to 9 cm, and advantageously a length in the range from about 6.5 to about 8.5 cm.

The brim is preferably a closed cell, substantially moisture impermeable polymeric foam having a thickness in the range from about 1 to 4 mm, and preferably about 2 to 3 mm.

The brim inner curved edge has a preferred radius of curvature in the range from about 8 to 15 cm, and preferably, each of said flaps extend approximately perpendicular to a line tangent to the curve of the inner brim edge at the point of intersection of the flap inner edge and said brim inner edge.

In use, the sun visor flaps are bent upwardly and are adapted to lie flat against the temples of the user, when the visor is secured to the head of the user by the band.

The sun visor brim member is produced by cutting a plurality of brims from a roll of stock material. The plurality of sun visor brims are formed from a first series of score lines for producing a first tandem series of visor brims, and a second series of score lines for producing a second tandem series of visor brims. The first series of score lines are nested within the second series of score lines, such that each flap member of said first series of visors has an inner edge which is proximate an inner edge of a flap member of a nested visor of the second series of visor brims.

DESCRIPTION OF THE PREFERRED EMBODIMENTS OF THE INVENTION

As illustrated in FIG. 1, the sun visor of the present invention, indicated generally as 100, includes two primary components, a visor section 110 and a bandanna 120. The visor has a brim region 114, which normally lies flat, but which forms a curved, characteristic brim shape, when worn. The bandanna 120 is secured to the visor 110 by a pair of flaps 112. While more than two flaps can be used, optimally only two are used in order to achieve the desired brim curvature. The use of additional flaps, as for example, a third centrally located flap provides additional support for the visor, and is particularly important when the visor is used in a windy environment, or in connection with an active sport, such as jogging or bike riding. The angle of the end flaps 112 serves to cause the flaps to interact with the bandanna when worn by the user, in such a manner as to cause the brim to arc in the desired characteristic shape.

The ends 122 and 124 of the bandanna are tied in a knot, as is well known, and illustrated for example, in FIGS. 1, 6 and 7.

As shown in FIG. 2, the end flaps when bent upwardly, and caused by the bandanna to curve to conform to the skull shape of the user, necessitates the brim to arc. When the end flaps are in the natural, folded or flat position, the visor 110 is flat, as illustrated in FIG. 5. FIGS. 5a and 5b, show the visor to lie flat, when separated from the bandanna.

The term "flap", as employed herein, is used to signify a flat, usually thin piece attached at only one side, a projecting piece intended to double over and cover.

As illustrated in FIG. 6, the bandanna 120 is rolled or folded and knotted in the manner characteristic of bandannas, and is placed on the flat visor. It is positioned such that it lies between the pairs of connector tabs 116 and 117, and 118 and 119. The connector tabs are preferably hook and loop connectors, such as sold under the trademark VELCRO. Other connectors can be used, such as snap connectors or buttons and buttonholes. Hook and loop connector can be a problem when attempting wash, in an automatic clothes washer, a product having such connectors. The problem arises from the tendency for the hook elements to catch lint and tangle with garments. Preferably, the visor is made of a flexible, self support sheet material, such as a closed cell polymeric foam. The preferred material is a vinyl polymer, formed from about 75% resin, 3% blowing agent, 1% cross-linking agent, about 0.5% stearic acid and about 20% fillers, such as clay, calcium carbonate, or combinations thereof. The material must be able to hold its shape in use, that is, must be self-supporting. Thus, the visor is not moisture absorbent and thus, does not require significant washing. Hand washing in soapy warm water is all that is needed to clean a soiled visor.

A material thickness of about 3 mm, is preferred. The minimum thickness is that which is consistent with a self supporting material, and the maximum thickness is consistent with cost and flexibility requirements. The combination of three flaps and a thickness of about 3 mm produces the desired self-supporting characteristics, with foamed vinyl plastics. Generally, a thickness range from 1 to 4 mm can be used.

In those instances where the visors are used in sporting activities such as running, jogging, biking and walking, the bandanna must serve as a sweat band and the visor flaps and inner edge of brim are subject to contact with perspiration. Consequently, the visor is preferably made of a material that does not absorb water and will not be stained by sweat from the brow of the user. The bandanna is readily washable, and the visor can be used with a plurality of different bandannas, scarves, or conventional elastic sweatbands. While the visor can readily be made of a natural or synthetic fabric, such as cotton, or wool, or nylon or polyester, the use of a plastic, closed cell foam is preferred, due to the water impermeability, and therefore minimizes or eliminates the need for frequent washing. The closed cell foam provides rigidity, that is, the ability to be self-supporting but still bend, at low cost and low weight.

As shown in FIG. 7, a first flap 112 is folded over such that the corresponding hook and loop elements 119 and 118, of FIGS. 6 and 7 engage and lock the flap around the knotted bandanna. Then, the second flap is folded over engaging the hook and loop elements 117 and 116.

The bandanna is then placed on the head of the user, with the visor component positioned at the user's forehead and the brim adapts to the required curved configuration.

The shape, or outline of the visor 110, must provide for the natural contouring of the visor when in use, and preferably additionally is a nestable contour, as illustrated in FIG. 4. As best seen in FIGS. 4 and 5, the flaps 112 project toward each other, from the base 141 of the flaps, to the ends 143 of the flaps. The flaps project approximately radially toward the center of the arc of curvature of the inner edge 150, of the visor 110. The outer edge 155 can be an arc segment of a circle that is concentric with the circle, of which edge 150 is an arc segment, or can be offset from the common center point, since the shape of the outer edge 155 is governed primarily by aesthetic considerations. The shape of the edge 155 is primarily determined by aesthetics requirements, while the contour of the inner edge 150 (when the brim is curved), must conform to the shape of the forehead of the average user.

When the flaps 112, are curved upwardly, they should conform to the curve of the inner edge 150, so that they will lie flat against the users forehead.

As shown in FIG. 4, the visors can be cut from a continuous roll of sheet material. The use of a continuous roll of sheet material is essential to minimize manufacturing costs and speed of production. Also essential to the economics of the system, is for the sun visor to have a contour such that adjacent visor patterns nest, thereby minimizing the amount of waste material which is produced during the cutting operation. As shown in FIG. 4, the flap 112 has its distal end 143 nested against the inner edge 350, of the visor pattern 310. The flaps 312 and 112 can, preferably, share a common line, but also, can be slightly offset, depending upon the cutting blade requirements. Similarly, the flaps 212 and 313, and 213 and 413, can share a common cutting line. The space which is created between the distal ends of the flaps and the inner edges of the mating visors, can be discard material, or the end of the flap can be contoured to conform the curvature of the brim inner edge.

As shown in FIG. 4A, the visor can be provided with a centrally positioned, radially inward extending flap. The flaps, as illustrated in FIG. 4A have the ends of the flaps mated against an inner edge of the mating visor pattern.

Figure 8:
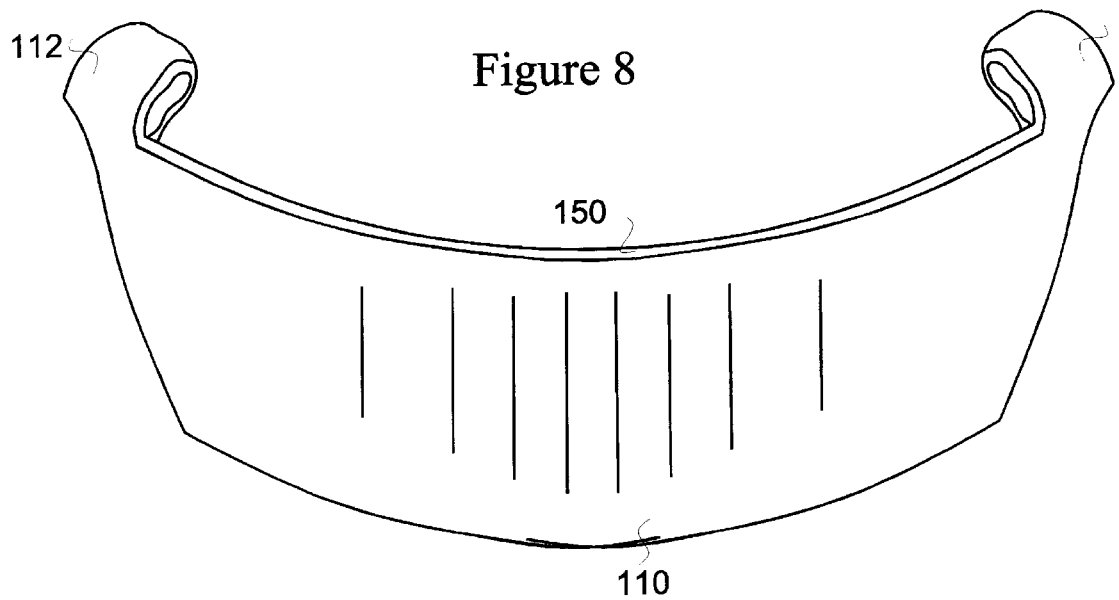
FIG. 8 is a top plan view of the sun visor, shown in the shape it takes when held against the forehead of the user.
Figure 9:
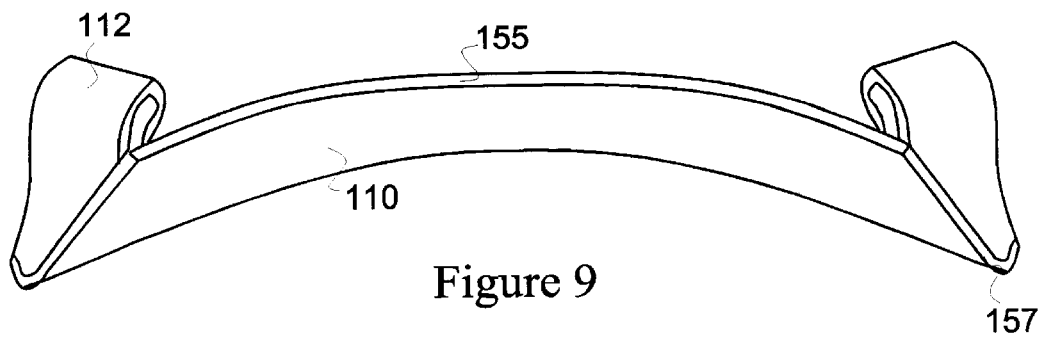
FIG. 9 is an upward front perspective view of the sun visor of FIG. 8, showing the curvature of the brim.
Figure 11:
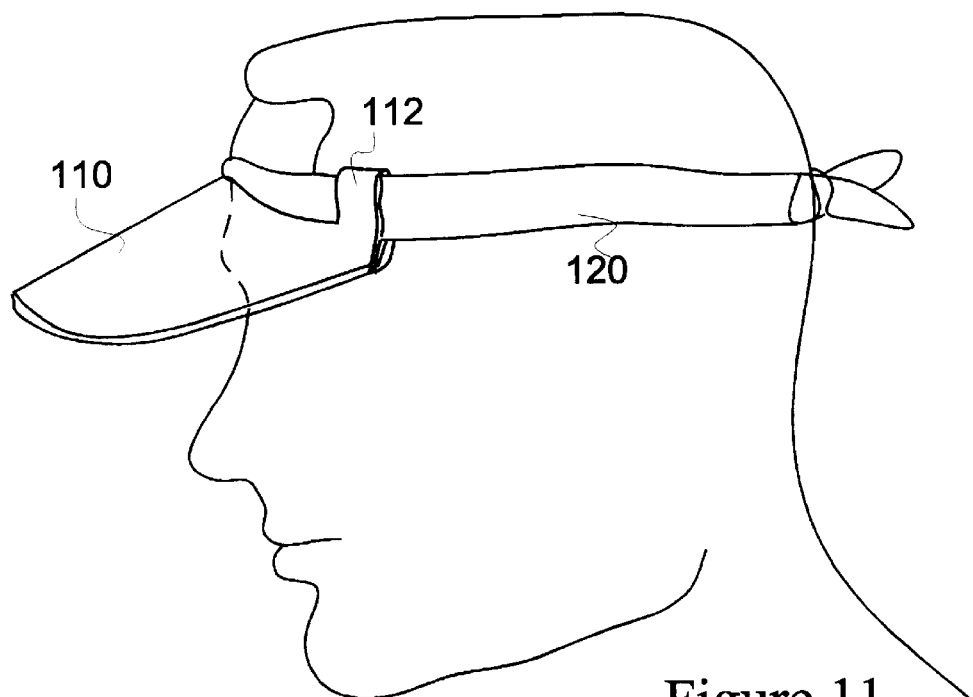
FIG. 11 is a side view of the sun visor of FIG. 8, shown on the head of a user.
Figure 12:
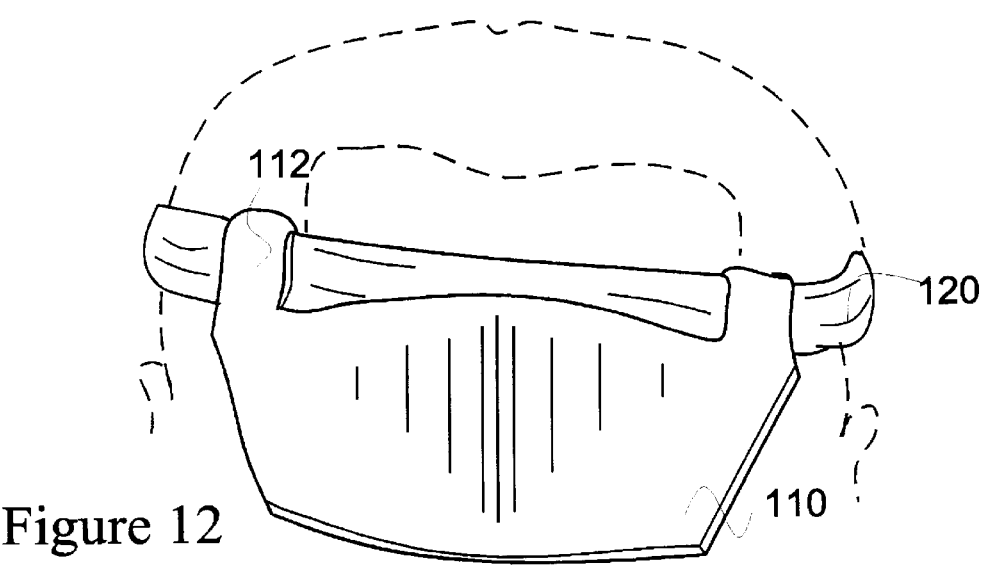
FIG. 12 is a front perspective view of the head band visor of FIG. 11.

As best seen in FIG. 9, the visor brim forms a curve when in use against the forehead of the user. As seen in FIG. 8, the flaps planar surface forms a continuation of the curve of the inner edge 150, of the brim 110. The dimensions and positioning of the user's forehead, is sufficiently long to releasable enclose a bandanna, and produce the brim curvature, characteristic of base ball caps and sun visors. It is noted that the flaps curve upwardly and are positioned to lie comfortably against the user's temples.

By way of contrast, attention is invited to the eye shield or sun visor of U.S. Pat. No. 1,809,956. The patent discloses a visor which has three loops, and can have loops spaced at any desired point on the visor. It is noted that the shape illustrated in FIG. 4 of the '956 patent, cannot be produced by the visor illustrated in FIG. 1. The loops, or eyes (2) of the '956 patent are not designed to curve upwardly and lie against the temples of the user. By way of contrast, as illustrated in FIGS. 1, and 11 to 14 of this invention, the flaps have a substantially elongated flat region which lies against the users head.

Also by way of contrast, attention is invited to U.S. Pat. No. 5,704,063 which discloses a structure for use as a face covering, and which bears a physical resemblance to the visor of the instant invention. However, the device could not work as a visor because the flaps indicated generally as 11, are not designed to lie flat against the forehead and the curvature of the central edge portion 10 is designed to conform to the curvature of the bridge of the nose region of the head of the user, and would not lie against the user's forehead.

EXAMPLE

A sun visor was cut from a rectangular piece of 2 mm self supporting vinyl closed cell foam, sold under the trademarks Darice Foamies, by Darice Inc., Strongsville, Ohio.

The visor was cut in the shape illustrated in FIG. 5. The inner brim edge 150 had a length of about 18 cm and the outer brim edge 155 had a length of 17.5 cm. The brim edges 156 and 157 had a length of about 9 cm each and the flap outer edges 160 had a length of 10 cm. The flap inner edges 162 had a length of 8.5 cm and the flap width was 3 cm. The distance between the brim inner edge 150 and outer edge 155, was 8 cm at the widest point. The radius of curvature of the arc of the inner brim edge 150 was 11.5 cm. The outer brim edge also had a radius of curvature of 11.5 cm. The dimensions of the outer brim edges 156, 157 and 155, are determined primarily by aesthetic considerations, while the inner brim edge 150 is determined by the requirement that when it is in the curved shape illustrated in FIG. 9, it conform to the shape of the human forehead. The hook and loops tabs were about 1 by 2 cm, but a different dimension, such as 0.5 cm by 2 cm could also be used. Where the nesting feature is desired or required, the width of the flaps is constrained by the nestable configuration, as illustrated in FIG. 4.

The flaps should be long enough to provide at least about a 2 cm space for the bandanna, and therefore should be at least about 5 cm in length, to accommodate the hook or loop patch. Because of the nesting feature, the flap length should be less than about 10 centimeters and preferably the flaps have a length in the range from about 6 to 9 cm. Most preferably, the flap length is in the range from about 8.5 to about 6.5 cm.

The radius of curvature of the inner brim edge can be in the range from about 8 to 15 cm, with the longer radius of curvature resulting in a deeper brim curvature as viewed in FIG. 9, and the shorter brim radius of curvature of the inner brim edge, producing a shallower brim curve. The flap inner edges 162 form, substantially, a right angle with a line which is tangent to the arc of the inner brim edge 150, at the point of intersection with the flap edge 162. By the term substantially, it should be understood that a deviation of up to about 10% can be used. The nesting feature places less constraint on the flaps being moved toward the position in which they are parallel to each other and a deviation of up to about 30% in this direction would not interfere with the nesting requirements. For convenience the deviation toward the position in which the flaps are parallel to each other will be termed "deviation toward the parallel" and deviation in the other direction will be termed "deviation away from the parallel". Deviation toward the parallel can be up to about 30% and deviation away from the parallel can be up to about 10%. A deviation of 10% being understood to be 9 degrees, and a deviation of 30% being 27 degrees.

What is claimed is:

1. A sun visor comprising the combination of a band of flexible, moisture absorbent material, a brim member, and a pair of fasteners, said brim member being a planar self supporting material, secured to said band, adapted to lie symmetrically curved when affixed to the head of a person by said band, and having an inner curved edge positioned to lie against the forehead of the user, when said brim member is affixed to the head of a person by said band, having at least a pair of flap members, each of said flap members extending radially inward from said curved inner edge and having a length in the range from about 5 cm to 10 cm, each of said pair of fasteners having a first element secured to each flap of said pair of flaps and positioned at the distal end of each flap, and a second element secured to said brim at a position adjacent to each flap, each flap being folded over with a first element engaging a second element, to form an elongated loop, said band being within each elongated loop and thereby secured to said brim.

2. The sun visor of claim 1, wherein said brim is a closed cell, substantially moisture impermeable polymeric foam.

3. The sun visor of claim 2, wherein said brim has a thickness in the range from about 1 to 4 mm.

4. The sun visor of claim 3, wherein said brim has a thickness of about 2 to 3 mm.

5. The sun visor of claim 1, wherein each flap has a length in the range from about 5 cm to about 10 centimeters.

6. The sun visor of claim 5, wherein each flap has a length in the range from about 6 to 9 cm.

7. The sun visor of claim 6, wherein each flap length is in the range from about 6.5 to about 8.5 cm.

8. The sun visor of claim 1, wherein said brim inner curved edge has a radius of curvature in the range from about 8 to 15 cm.

9. The sun visor of claim 1, wherein each of said flaps extend approximately perpendicular to a line tangent to the curve of the inner brim edge at the point of intersection of the flap inner edge and said brim inner edge.

10. The sun visor of claim 1, wherein each of said flaps extend away from said brim inner edge, radially inward, and deviate from a first line which is perpendicular to a second line tangent to the curve of the inner brim edge at the point of intersection of the flap inner edge and said brim inner edge, said deviation being up to thirty percent.

11. The sun visor of claim 10, wherein said deviation is up to about 10%.

12. The sun visor of claim 10, wherein said deviation is up to about 10% away from parallel.

13. The sun visor of claim 1, wherein said brim is a closed cell, substantially moisture impermeable polymeric foam, has a thickness in the range from about 1 to 4 mm, said brim inner curved edge has a radius of curvature in the range from about 8 to 15 cm, and each of said flaps extend away from said brim inner edge, radially inward, and deviate from a first line which is perpendicular to a second line tangent to the curve of the inner brim edge at the point of intersection of the flap inner edge and said brim inner edge, said deviation being up to thirty percent.

14. The sun visor of claim 13, wherein said brim has a thickness of about 2 to 3 mm, each flap length is in the range from about 6.5 to about 8.5 cm, and wherein each of said flaps extend away from said brim inner edge, radially inward, and deviate from a first line which is perpendicular to a second line tangent to the curve of the inner brim edge at the point of intersection of the flap inner edge and said brim inner edge, said deviation being up to thirty percent toward the parallel and up to about 10% away from parallel.

15. The sun visor of claim 1, wherein the flaps are curved upwardly and are adapted to lie flat against the temples of the user, when the visor is secured to the head of the user by the band.

16. A visor comprising, in combination, a visor body member and a fabric band member, said visor body member being a dense flexible foam member, said body member having flap at each end, each flap having a first fastener at its distal end and said body member having a cooperating fastener positioned to interact with said first fastener when said flap is in a folded position, said first fastener and said cooperating fastener being hook and loop elements, said fabric band member being of a sweat absorbing, washable fabric, each said flap being folded around said fabric member, said visor body member being adapted to being secured to the head of a person by said fabric band member.

* * * * *